US012623995B2

(12) United States Patent
Choi et al.

(10) Patent No.: US 12,623,995 B2
(45) Date of Patent: May 12, 2026

(54) METHOD OF PREPARING HETEROGENEOUS LINEAR CARBONATE USING AMINE-BASED COMPOUND CATALYST

(71) Applicant: LOTTE CHEMICAL CORPORATION, Seoul (KR)

(72) Inventors: Jong Myung Choi, Daejeon (KR); Mi Hwa Baek, Daejeon (KR); Wang Gyu Kim, Daejeon (KR); Eun Hye Han, Daejeon (KR); Jin Hyung Kim, Daejeon (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 419 days.

(21) Appl. No.: 18/254,010

(22) PCT Filed: Nov. 4, 2021

(86) PCT No.: PCT/KR2021/015846
§ 371 (c)(1),
(2) Date: May 23, 2023

(87) PCT Pub. No.: WO2022/114577
PCT Pub. Date: Jun. 2, 2022

(65) Prior Publication Data
US 2023/0406809 A1      Dec. 21, 2023

(30) Foreign Application Priority Data
Nov. 26, 2020      (KR) ........................ 10-2020-0161740

(51) Int. Cl.
*C07C 68/06* (2020.01)
*B01J 31/02* (2006.01)
*B01J 31/06* (2006.01)

(52) U.S. Cl.
CPC ........... *C07C 68/06* (2013.01); *B01J 31/0238* (2013.01); *B01J 31/068* (2013.01); *B01J 2231/49* (2013.01); *C07C 2531/06* (2013.01)

(58) Field of Classification Search
CPC .... C07C 68/06; C07C 2531/06; B01J 31/068; B01J 2231/49
See application file for complete search history.

(56) References Cited

FOREIGN PATENT DOCUMENTS

| | | | |
|---|---|---|---|
| CN | 1597113 | A | 3/2005 |
| CN | 100435951 | C | 11/2008 |
| JP | H0710811 | A | 1/1995 |
| JP | H11514010 | A | 11/1999 |
| JP | 3340188 | B2 | 11/2002 |
| JP | 2010120011 | A | 6/2010 |
| JP | 2017521422 | A | 8/2017 |
| KR | 10-2011-0090827 | A | 8/2011 |
| KR | 101668571 | B1 | 10/2016 |
| WO | 03006418 | A1 | 1/2003 |

OTHER PUBLICATIONS

Office Action issued in corresponding Japanese Patent Application No. 2023-532180 dated Apr. 23, 2024 (4 pages).
Extended European Search Report issued in European Application No. 21898403.7, dated Jan. 15, 2025 (7 pages).
Office Action issued in Korean Application No. 10-2020-0161740; Dated Oct. 17, 2024 (5 pages).
International Search Report issued for corresponding international patent application No. PCT/KR2021/015846, mailed Feb. 23, 2022 (5 pages).
Written Opinion issued for corresponding international patent application No. PCT/KR2021/015846, mailed Feb. 23, 2022 (4 pages).
Tobias Keller, et al., "Transesterification of Dimethyl Carbonate with Ethanol to Form Ethyl Methyl Carbonate and Diethyl Carbonate: A Comprehensive Study on Chemical Equilibrium and Reaction Kinetics;" Industrial & Engineering Chemistry Research; Sep. 1, 2011, vol. 50, pp. 11073-11086 (14 pages).
Tobias Keller, et al., "Transesterification of dimethyl carbonate with ethanol in a pilot-scale reactive distillation column;" Chemical Engineering Journal; 2012, vol. 180, pp. 309-322 (14 pages).

*Primary Examiner* — Alicia L Otton
(74) *Attorney, Agent, or Firm* — Osha Bergman Watanabe & Burton LLP

(57) ABSTRACT

The present invention is directed to providing a method of preparing a heterogeneous linear carbonate, including: performing a transesterification reaction of dimethyl carbonate (DMC) and ethanol (EtOH) in the presence of a catalyst, wherein the catalyst is an amine-based compound having a boiling point of 150° C. or more.

5 Claims, No Drawings

METHOD OF PREPARING HETEROGENEOUS LINEAR CARBONATE USING AMINE-BASED COMPOUND CATALYST

TECHNICAL FIELD

The present invention relates to a method of preparing a heterogeneous linear carbonate using an amine-based compound catalyst.

BACKGROUND ART

It is well known that a method of preparing ethyl methyl carbonate (EMC) and diethyl carbonate (DEC), which are used as organic solvents for battery electrolytes is through a transesterification reaction of dimethyl carbonate (DMC) and ethanol.

At this time, a catalyst is used for the reaction, and as the catalyst, sodium methoxide (NaOCH₃, SME) and sodium hydroxide (NaOH), which have excellent activity, are mainly used.

However, since the SME or NaOH has low solubility in organic solvents and is insoluble in DMC, EMC, and DEC, it causes column plugging in a reactive distillation process or a purification process, so that process trouble occurs.

In this regard, Patent Document 1 discloses that DEC is produced at a high rate by utilizing the SME catalyst, which is a basic homogeneous catalyst, and reactive distillation. However, in this case, the catalyst may pass into the distillation system and cause a reverse reaction during the distillation process, or may be precipitated to block a pipe or adsorbed inside the distillation column to cause corrosion.

Accordingly, Patent Document 2 discloses that DEC was prepared using a strongly basic anion exchange resin as a heterogeneous catalyst instead of using SME as a basic homogeneous catalyst, thereby facilitating the separation of a reaction product and a catalyst, however, productivity is low due to insufficient catalytic activity. In addition, product production has to be stopped periodically and the catalyst needed to be regenerated due to the catalyst deactivation problem, which further lowers product productivity and increases production costs.

Therefore, there is a need for research on a method for effectively preparing a heterogeneous linear carbonate for a battery electrolyte by solving the above problems.

RELATED ART DOCUMENTS

Patent Document (Patent Document 1) Korean Patent Publication No. 10-1668571
(Patent Document 2) Japanese Patent Publication No. 3340188

DISCLOSURE

Technical Problem

The present invention provides a method of preparing a heterogeneous linear carbonate, wherein since the method uses an amine-based compound with a relatively high boiling point as a catalyst, which has better catalytic activity than basic anion exchange resins and can obtain high productivity, and a catalyst precipitation problem does not occur, and a desired compound can be easily separated by distillation due to the large boiling point difference, the desired compound can be obtained in excellent yield.

Technical Solution

One embodiment of the present invention provides a method of preparing a heterogeneous linear carbonate, the method including performing a transesterification reaction of dimethyl carbonate (DMC) and ethanol (EtOH) in the presence of a catalyst, wherein the catalyst is an amine-based compound having a boiling point of 150° C. or more.

Advantageous Effects

In a method of preparing a heterogeneous linear carbonate according to the present invention, by using an amine-based compound having a relatively high boiling point as a catalyst, catalytic activity is superior to that of the basic anion exchange resin, and there is no problem of stopping production due to catalyst regeneration, so that higher productivity can be obtained.

In addition, when the amine-based compound having a high boiling point is used, it is well soluble in dimethyl carbonate, diethyl carbonate, ethyl methyl carbonate, and ethanol, so that catalyst precipitation problems do not occur, and as a result, since the boiling point difference from synthesized diethyl carbonate and ethyl methyl carbonate is large, they can be easily separated through distillation, so that a desired compound can be obtained in excellent yield.

Furthermore, according to the present invention, by using a CSTR for the transesterification reaction, it is easy to adjust a production ratio of the desired heterogeneous linear carbonate through adjusting a ratio of dimethyl carbonate and ethanol as raw materials.

MODES OF THE INVENTION

Throughout the specification, when a part is said to "include" a component, this means that the part may further include other components rather than excluding other components unless specifically stated to the contrary.

In the present specification, the unit "% by weight" may mean the ratio of the weight of a certain component to total components.

Hereinafter, the present invention will be described in detail.

One embodiment of the present invention provides a method of preparing a heterogeneous linear carbonate, the method including performing a transesterification reaction of dimethyl carbonate (DMC) and ethanol (EtOH) in the presence of a catalyst,
wherein the catalyst is an amine-based compound having a boiling point of 150° C. or more.

In the present invention, the heterogeneous linear carbonate means a species of carbonate which is different from dimethyl carbonate, specifically, an asymmetric linear carbonate and a symmetric linear carbonate, and more specifically, ethyl methyl carbonate (EMC) and diethyl carbonate (DEC).

Examples of catalysts conventionally used in a transesterification reaction include lithium methoxide (LME), lithium ethoxide (LEE), sodium methoxide (SME), sodium hydroxide (NaOH) and a mixture thereof.

However, as described above, these catalysts have low solubility in organic solvents and do not dissolve in dimethyl carbonate as a reaction raw material, ethyl methyl carbonate or diethyl carbonate as a desired product, so that there was a problem of causing column plugging in a reaction process or a purification process.

In addition, a technique of using a basic anion exchange resin as a catalyst has been proposed to solve this problem, but the basic anion exchange resin has a problem of low productivity due to insufficient catalytic activity.

Accordingly, the inventors of the present application, as a result of in-depth contemplation of how to effectively solve this problem, found that when an amine-based compound is used as a catalyst, the amine-based catalyst is well soluble in carbonate materials and ethanol, and it was confirmed that catalytic activity is also increased without a problem of catalyst precipitation, and the present invention was completed.

However, even when the amine-based compound is used as a catalyst, there is a fatal disadvantage that an amine-based compound having a low boiling point is difficult to separate from a desired compound synthesized in a subsequent distillation process.

Therefore, the amine-based compound used as the catalyst according to the present invention should have a boiling point of at least 150° C. or more, and specifically, it is preferable that the boiling point of the amine-based compound is 150° C. or more and 400° C. or less, more specifically, 200° C. or more and 300° C. or less.

The amine-based compound having a boiling point of 150° C. or more is not limited when the above conditions are satisfied, but may be one or more selected from the group consisting of, for example, 1,6-diaminohexane, 1,8-diaminooctane, 1,9-diaminononane, diethanolamine, triethanolamine, polyetheramine (PEA) and a mixture thereof, and specifically, polyetheramine (PEA).

A molecular weight of the amine-based compound is not particularly limited, but a weight average molecular weight may be 150 g/mol or more and 500 g/mol or less, specifically, 200 g/mol or more and 400 g/mol or less, more specifically 200 g/mol or more and 300 g/mol or less.

The weight average molecular weight was measured using gel permeation chromatography (GPC), and specifically, evaluated using a Waters PL-GPC220 instrument using a PL aquagel-OH 30-40 column, which is 300 mm long. An evaluation temperature was 30° C., 0.1 M NaNO₃ in distilled water was used as a solvent, and measurement was performed at a flow rate of 1 mL/min. Samples were prepared at a concentration of 10 mg/10 mL, and then supplied in an amount of 15 μL. An Mw value was derived using a calibration curve formed using polystyrene standards. For the molecular weights of polyethylene glycol standards, nine types of 2,000/10,000/30,000/70,000/200,000/700,000/2,000,000/4,000,000/10,000,000 were used. Alternatively, a molecular weight distribution was measured using a rotational rheometer and GPC. In addition, as the structural parameters of the sample, a weight ratio (Wt) of a comb polymer and a weight average molecular weight (Mw) of the main chain were selected as a branched polymer structure in the amine-based compound.

When the weight average molecular weight is less than 150 g/mol, which is below the range, the reaction between the catalyst and dimethyl carbonate as a reactant, may increase an amount of by-product production, and when the weight average molecular weight exceeds 500 g/mol, which is above the range, the catalyst activity is too low, and flowability is lowered due to a viscosity increase, which may reduce process efficiency.

In this aspect, it is most preferable that polyetheramine (PEA) having the above weight average molecular weight is used as a catalyst.

In addition, an amount of these catalysts may be 0.1% by weight or more and 30% by weight or less, specifically 1% by weight or more and 20% by weight or less, and more specifically 5% by weight or more and 10% by weight or less, based on the weight of dimethyl carbonate.

When the content is below the above range, the catalyst activity is too low and productivity is lowered, and when the content exceeds the above range, the amount of input catalyst is increased even though an amount of unused catalyst is large, which is not preferable in terms of economics.

In the case of using such an amine-based compound, catalyst precipitation can be prevented by solving a conventional problem, and a productivity decrease can be prevented by increasing catalytic activity.

Meanwhile, dimethyl carbonate included as a reaction raw material may be purchased and used commercially, and may be those obtained by a gas phase catalytic reaction of carbon monoxide and nitrite ester, those obtained by reacting carbon dioxide and an alcohol under a solid catalyst, and dimethyl carbonate produced by a known method.

As another reaction raw material, commercially available ethanol may be used as it is, but it is preferable to use ethanol having a moisture content of 0.20% by mass or less (2000 ppm or less) so as not to affect the transesterification reaction of the present invention. Here, the removal of the contained water is performed by dehydration operation or the like with a drying agent such as, for example, a molecular sieve, anhydrous magnesium sulfate and/or calcium oxide.

An amount of ethanol used may be 50% by weight or more and 150% by weight or less, specifically, 80% by weight or more and 130% by weight or less, more preferably 100% by weight or more and 130% by weight or less, based on the weight of dimethyl carbonate.

When the amount of input ethanol is too small, the reaction does not proceed efficiently, meanwhile, when the input amount is too much, the complexity of removing the ethanol after the reaction increases, and is also not preferable in terms of economics.

Furthermore, an essential transesterification reaction in preparation of the heterogeneous linear carbonate according to the present invention, that is, ethyl methyl carbonate and diethyl carbonate, may be performed in a continuous stirred tank reactor (CSTR).

Specifically, in the CSTR, the dimethyl carbonate and ethanol undergo an exchange reaction in the presence of a transesterification catalyst, from which a desired product can be obtained. More specifically, when dimethyl carbonate, ethanol, and the catalyst, which are raw materials for preparation, are continuously supplied to the CSTR, reaction products produced in the reactor are discharged as an effluent stream, and then put into a distillation column to selectively separate and obtain ethyl methyl carbonate and diethyl carbonate as desired products.

At this time, a reaction temperature of the transesterification reaction is affected by the temperature in the CSTR, which is a reactor. The reaction temperature may be 30° C. or more and 130° C. or less, and specifically, may be adjusted to 60° C. or more and 120° C. or less.

When the reaction temperature is below the above range, the reaction is not easily performed and reaction efficiency is low, and when the temperature exceeds the above range, there is a problem in that the yield is lowered and separation and purification of the product becomes difficult due to the increase in side reactants, which are not desirable.

In addition, the pressure of the reaction is not particularly limited, and may vary depending on the reaction temperature and reaction composition, and may be, for example, normal pressure to 1000 kPa.

In addition, the pH of the reaction is maintained in the range of 6 or more and 9 or less. An alkali metal compound or alkaline earth metal compound may be added to the reaction when necessary to maintain the pH. Exemplary alkaline earth metal compounds include, but are not limited to, oxides, hydroxides, carbonates, and carboxylic acid salts.

The reaction time varies depending on reaction conditions, reaction raw materials, and other factors that may affect the reaction. Typically, however, the reaction time is between 0.5 and 20 hours. In the case of a continuous process using a CSTR, the reaction time (retention time) is determined by the kinetics of a system, which is determined by the used pressure, temperature and catalyst.

Thus, conditions of a transesterification reaction by a CSTR includes the reaction pressure, temperature, concentrations of the reactants, pH, and reaction time suitable to produce a desired reaction product. Any specific conditions used in this process are not particularly limited and are selected based on the reaction raw materials and composites produced using the process.

In this way, when the transesterification reaction is completed using the CSTR, the reaction concentrate and the composite including ethyl methyl carbonate and diethyl carbonate are obtained as an effluent stream. In addition, when this is filtered through a filter and then subjected to distillation, high purity ethyl methyl carbonate and diethyl carbonate can be obtained in excellent yield without catalyst precipitation.

In the case of using the CSTR in this way, it is easy to adjust a production ratio of the desired heterogeneous linear carbonate through adjusting ratios of dimethyl carbonate and ethanol, which are raw materials.

Hereinafter, examples will be given to describe the present invention specifically. However, the examples according to the present invention may be modified in various other forms, and the scope of the present invention is not to be construed as being limited to the examples described below. The examples of the present specification are provided to more completely explain the present invention to those of ordinary skill in the art.

Example 1

135 g of dimethyl carbonate (DMC) and 104 g of ethanol (EtOH) were put into a glass reactor with a volume of 500 mL and mixed, polyetheramine (PEA, weight average molecular weight: 230 g/mol) as a catalyst was put into the glass reactor at 1 wt % based on the weight of DMC, mixed while stirring at 500 rpm, the temperature was raised to 70° C. under 1 bar, and maintained for 1 hour to synthesize ethyl methyl carbonate and diethyl carbonate.

After the reaction was completed, the temperature of the reactor was cooled to room temperature, and then a composite was recovered from the reactor and passed through a filter made of PTFE having an average pore diameter of 450 nm to remove solid precipitates.

Example 2

Ethyl methyl carbonate and diethyl carbonate were synthesized in the same manner as in Example 1, and solid precipitates were removed through a filter, except that, in Example 1, polyetheramine as a catalyst was put into a glass reactor at 5 wt % based on the weight of DMC.

Example 3

Ethyl methyl carbonate and diethyl carbonate were synthesized in the same manner as in Example 1, and solid precipitates were removed through a filter, except that, in Example 1, polyetheramine (PEA, weight average molecular weight: 400 g/mol) as a catalyst was put into a glass reactor.

Example 4

Ethyl methyl carbonate and diethyl carbonate were synthesized in the same manner as in Example 1, and solid precipitates were removed through a filter, except that, in Example 1, polyetheramine (PEA, weight average molecular weight: 400 g/mol) as a catalyst was put into a glass reactor at 5 wt % based on the weight of DMC.

Comparative Example 1

Ethyl methyl carbonate and diethyl carbonate were synthesized in the same manner as in Example 1, and solid precipitates were removed through a filter, except that, in Example 1, a strong basic ion exchange resin (TRILITE MA-120H) instead of polyetheramine as a catalyst was put into a glass reactor at 5 wt % based on the weight of DMC.

Comparative Example 2

Ethyl methyl carbonate and diethyl carbonate were synthesized in the same manner as in Example 1, and solid precipitates were removed through a filter, except that, in Example 1, sodium methoxide (SME) instead of polyetheramine as a catalyst was put into a glass reactor at 1 wt % based on the weight of DMC.

Experimental Example 1

Qualitative and quantitative analyses were performed on the consumption amount of dimethyl carbonate as a raw material for preparation and production amounts of ethyl methyl carbonate and diethyl carbonate as desired products in Examples 1 to 4 and Comparative Examples 1 and 2, and results are shown in Table 1 below.

For the qualitative and quantitative analyses, 1 g of a product passed through the filter was taken and mixed with 0.1 g of m-xylene, and then the concentration was measured using gas chromatography (GC) (YL6500GC manufactured by YOUNG IN Chromass Co., GC column: DB-1 30 m×0.53 mm, GC detector: FID). In addition, a reaction conversion rate of dimethyl carbonate as a raw material for preparation was calculated as mol % based on a consumption amount compared to an amount used, and the reaction selectivity of ethyl methyl carbonate as a desired product was calculated as mol % of a content of ethyl methyl carbonate relative to a total content of ethyl methyl carbonate and diethyl carbonate respectively produced.

In addition, the concentration of the precipitate was measured by the difference between a weight of the filter before passing a composite through the filter and a weight of the filter after passing the composite, and the results are also shown in Table 1 below.

TABLE 1

| Classification | | Example 1 | Example 2 | Example 3 | Example 4 | Comparative Example 1 | Comparative Example 2 |
|---|---|---|---|---|---|---|---|
| Activity results | DMC conversion rate [%] | 10 | 34 | 7 | 28 | 6 | 65 |
| | EMC selectivity [%] | 90 | 86 | 91 | 87 | 92 | 74 |
| Solid precipitate concentration [ppm] | | 0 | 0 | 0 | 0 | 15 | 418 |

Referring to Table 1, when prepared according to the present invention, it can be confirmed that the catalyst is not precipitated at all compared to Comparative Example 2.

Therefore, it is possible to completely solve the plugging problem caused by catalyst precipitation. Meanwhile, compared to Comparative Example 1, it can be confirmed that when an amine-based compound according to the present invention is used as a catalyst, catalytic activity is higher and a DMC conversion rate is higher than when a strong basic ion exchange resin is used.

In addition, when comparing Example 1 and Example 3, and Example 2 and Example 4, it can be confirmed that the activity decreases as a molecular weight of the catalyst increases, so that it is preferable to select a catalyst having an appropriate weight average molecular weight.

In addition, referring to Examples 1 and 2, and Examples 3 and 4, the greater the weight of the catalyst, the better the activity, so that it is more preferable to include 5 wt % or more of the catalyst.

The invention claimed is:

1. A method of preparing a heterogeneous linear carbonate, comprising performing a transesterification reaction of dimethyl carbonate (DMC) and ethanol (EtOH) in the presence of a catalyst,
   wherein the catalyst is an amine-based compound comprising polyetheramine (PEA) having a boiling point of 150° C. or more.

2. The method of claim 1, wherein the catalyst has a boiling point of 150° C. or more and 400° C. or less.

3. The method of claim 1, wherein the amine-based compound has a weight average molecular weight of 150 g/mol or more and 500 g/mol or less.

4. The method of claim 1, wherein the catalyst is added in an amount of 0.1% by weight or more and 30% by weight or less based on a weight of the dimethyl carbonate.

5. The method of claim 1, wherein the transesterification reaction is performed in a continuous stirred tank reactor (CSTR).

* * * * *